United States Patent
Buffe et al.

(12) 
(10) Patent No.: US 10,174,152 B2
(45) Date of Patent: Jan. 8, 2019

(54) PROCESS FOR PRODUCING ISOHEXIDE GLYCIDYL ETHERS, PRODUCTS THUS OBTAINED, AND USES THEREOF

(71) Applicant: ROQUETTE FRERES, Lestrem (FR)

(72) Inventors: Clothilde Buffe, Lomme (FR); Amelie Dolenec, Beuvry (FR); Mathias Ibert, La Chapelle d'Armentieres (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 15/113,078

(22) PCT Filed: Jan. 21, 2015

(86) PCT No.: PCT/FR2015/050148
§ 371 (c)(1),
(2) Date: Jul. 21, 2016

(87) PCT Pub. No.: WO2015/110758
PCT Pub. Date: Jul. 30, 2015

(65) Prior Publication Data
US 2017/0002132 A1    Jan. 5, 2017

(30) Foreign Application Priority Data
Jan. 21, 2014    (FR) .................................... 14 50474

(51) Int. Cl.
| | | |
|---|---|---|
| C07D 493/04 | (2006.01) | |
| C08G 59/26 | (2006.01) | |
| C08G 59/50 | (2006.01) | |

(52) U.S. Cl.
CPC ........... *C08G 59/26* (2013.01); *C07D 493/04* (2013.01); *C08G 59/5026* (2013.01)

(58) Field of Classification Search
CPC ................................................... C07D 493/04
See application file for complete search history.

(56) References Cited

U.S. PATENT DOCUMENTS

| | | |
|---|---|---|
| 3,041,300 A | 6/1962 | Morrison |
| 3,272,845 A | 9/1966 | Zech et al. |
| 4,770,871 A | 9/1988 | Greenshields |
| 2014/0073716 A1 | 3/2014 | Cho et al. |

FOREIGN PATENT DOCUMENTS

| | | | | |
|---|---|---|---|---|
| EP | 2 301 941 A1 | 3/2011 | | |
| EP | 2301941 A1 * | 3/2011 | ........... | C07D 493/04 |
| WO | 2008/147472 A1 | 12/2008 | | |
| WO | 2008/147473 A1 | 12/2008 | | |
| WO | WO 2008147472 A1 * | 12/2008 | ............... | C07H 1/00 |
| WO | WO-2011029548 A1 * | 3/2011 | ........... | C07D 493/04 |
| WO | 2012/157832 A1 | 11/2012 | | |

OTHER PUBLICATIONS

IUPAC. "Alkyl Groups." © 2017. Available from: < http://goldbook.iupac.org/html/A/A00228.html >.*
IUPAC. "Cycloalkyl Groups." © 2017. Available from: < http://goldbook.iupac.org/html/C/C01498.html >.*
Versace, et al.: "A Tris(triphenylphosphine)ruthenium(II) Complex as a UV Photoinitiator for Free-Radical Polymerization and in Situ Silver Nanoparticle Formation in Cationic Films", Macromolecules, vol. 46, No. 22, Nov. 26, 2013, (Nov. 26, 2013), pp. 8808-8815, XP055112129, ISSN: 0024-9297, DOI: 10.1021/ma4019872.
Chatti, et al.: "Cation and leaving group effects in isosorbide alkylation under microwave in phase transfer catalysis", Tetrahedron, Elsevier Science Publishers, Amsterdam, NL, vol. 57, No. 20, May 14, 2001 (May 14, 2001), pp. 4365-4370, XP004239462, ISSN: 0040-4020, DOI: 10.1016/S0040-4020(01)00318-0.
Ratuer, et al.: "Determination of Bisphenol A diglycidyl ether (BADGE) and its hydrolysis products in canned oily foods from the Austrian market", Z. Lebensm, Unters. Forsch. A, vol. 208, 1999, pp. 208-211.
International Search Report, dated Mar. 19, 2015, from corresponding PCT Application.

* cited by examiner

*Primary Examiner* — Andrew D Kosar
*Assistant Examiner* — John S Kenyon
(74) *Attorney, Agent, or Firm* — Oliff PLC

(57) ABSTRACT

A process for producing bis-anhydrohexitol ether compositions and in particular isohexide glycidyl ether compositions, one of the originalities of which is azeotropic distillation carried out under reduced pressure. Such compositions are used to produce epoxy resins, the function thereof being to form a three-dimensional macromolecular network. The compositions obtained according to the process are rich in diepoxy derivatives of isosorbide to the detriment of monoepoxy derivatives, only the first participating in the formation of the three-dimensional network. The crosslinking density is therefore increased, thereby making it possible to obtain a material which is more chemically resistant and mechanically stronger and which has a higher glass transition temperature (Tg), compared with the same materials obtained with bis-anhydrohexitol ether compositions according to the prior art.

9 Claims, No Drawings

PROCESS FOR PRODUCING ISOHEXIDE GLYCIDYL ETHERS, PRODUCTS THUS OBTAINED, AND USES THEREOF

The main subject of the present invention is a process for producing a bis-anhydrohexitol ether composition and in particular an isohexide glycidyl ether composition, one of the originalities of which is based on azeotropic distillation carried out under reduced pressure. Such compositions, products are used to produce epoxy resins, the function thereof being to form a three-dimensional macromolecular network. The compositions obtained according to the process which is the subject of the invention are rich in diepoxy derivatives of isosorbide to the detriment of monoepoxy derivatives, only the first participating in the formation of the three-dimensional network. The crosslinking density is therefore increased, thereby making it possible to obtain a material which is more chemically resistant and mechanically stronger and which has a higher glass transition temperature (Tg), compared with the same materials obtained with the bis-anhydrohexitol ethers according to the prior art.

A subject of the present invention is also the bis-anhydrohexitol ether compositions thus produced, and also the use thereof in the production of composite materials, of coatings or else of adhesives.

The bisphenol A glycidyl ether (BADGE or DGEBA), of formula (I), is a chemical compound used as a crosslinking agent in the production of epoxy resins. This product today appears on the list of carcinogens of group 3 of the IARC (International Agency for Research on Cancer), i.e. it is a substance that is unclassifiable with regard to its carcinogenicity for humans.

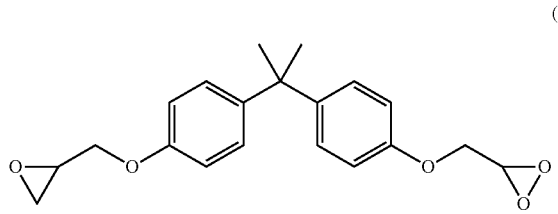
(I)

However, DGEBA is in particular used as an additive in coatings for some cans of food. Free DGEBA can therefore be found in the content of these cans, thereby feeding numerous questions regarding its carcinogenicity ("Determination of Bisphenol A diglycidyl ether and its hydrolysis products in canned oily foods from the Austrian market", Z. Lebensm, Unters. Forsch. A 208 (1999) pp. 208-211).

It has been known for a few years that this product can be replaced with isosorbide glycidyl ether, the structure of which is represented below (formula (II)). This structure mimics very closely that of DGEBA.

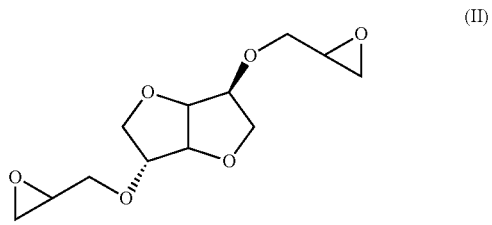 [SMILES: C1OC1CO[C@H]1COC2C1OC[C@H]2OCC1CO1]
(II)

These compounds, which belong to the more general class of bis-anhydrohexitol ethers, are today widely known and described in the literature, as is the process for synthesizing them.

One of the known synthesis processes is based on the initial formulation of a solution of an isohexide salt in the presence of very reactive and often dangerous species, such as sodium hydride or sodium metal, and then on reaction with epichlorohydrin. Document U.S. Pat. No. 3,272,845 is an illustration thereof.

Document U.S. Pat. No. 4,770,871 proposes an alternative method, which avoids making use of the metal hydride or the sodium metal. This method consists in reacting a bis-anhydrohexitol and an alkyl carbonate in the presence of a basic catalyst, and under high temperature and pressure conditions (200 to 300° C., 5 MPa).

Document WO 2008/147472 is also known, which describes another process not using the abovementioned dangerous compounds. This document proposes a method of synthesis by dissolving an isohexitol in a solvent, adding a base, carrying out an azeotropic distillation with the solvent, adding a compound chosen from the group consisting of an alkyl halide or aralkyl halide, and a sulfonate ester of the alcohol equivalent to the alkoxide, and heating in order to carry out the etherification reaction and to obtain the desired product. The solvents used are aromatic solvents, such as toluene and benzene. These solvents are not at home with the current regulations which aim to limit the use of these compounds that are often harmful and sometimes even toxic.

Document U.S. Pat. No. 3,041,300, for its part, proposes a method which does not make use of solvents, nor of metal hydride or of sodium metal. The process in question consists in reacting the isosorbide and epichlorohydrin at atmospheric pressure and under hot conditions (approximately 110° C.), in very slowly adding a basic reagent such as a sodium hydroxide solution (over the course of at least 4 hours), and in carrying out an azeotropic distillation. After filtration and rinsing, the bis-anhydrohexitol ether thus formed is then recovered. More recently, document WO 2012/157832 proposes a variant of this technique, by this time carrying out the reaction between the isosorbide and the epichlorohydrin still under atmospheric pressure but at a more moderate temperature (40° C.)

Finally, document WO 2008/147473 describes 3 of the previous processes:
  in its example 1, the method based on an azeotropic distillation in the presence of solvent according to document WO 2008/147472,
  in its example 2, the method using sodium hydride according to document U.S. Pat. No. 3,272,845,
  in its example 4, the method based on the very slow addition of sodium hydroxide and azeotropic distillation according to documents U.S. Pat. No. 3,041,300 and WO 2012/157832.

This document WO 2008/147473 teaches another route, which is a 2-step process, the first consisting in reacting isohexitol with epichlorohydrin in the presence of boron trifluoride, then in adding an alkaline solution (example 3 of this document). Nevertheless, it is known that boron trifluoride is a colorless toxic gas which reacts with moist air to form white fumes composed of hydrogen fluoride, of boric acid and of fluoroboric acid.

When any one of the previously described processes is carried out, a composition (as opposed to a pure product) containing in particular monofunctional and difunctional derivatives of bis-anhydrohexitol ethers is in fact obtained.

However, only said difunctional derivatives participate in the three-dimensional macromolecular network during the production of resin, in particular in the presence of curing agents of amine type. It is therefore these difunctional derivatives that it will be sought to favor to the detriment of the monofunctional products.

In the same way, care will be taken to limit the content of oligomer (III) in order to obtain a three-dimensional network having a higher crosslinking density. Indeed, the greater the value of n, the greater the distance between 2 reactive functions and therefore the greater the distance between each crosslinking node. A high node density makes it possible to obtain a material which has a higher glass transition temperature (Tg) and which is more chemically resistant and mechanically stronger.

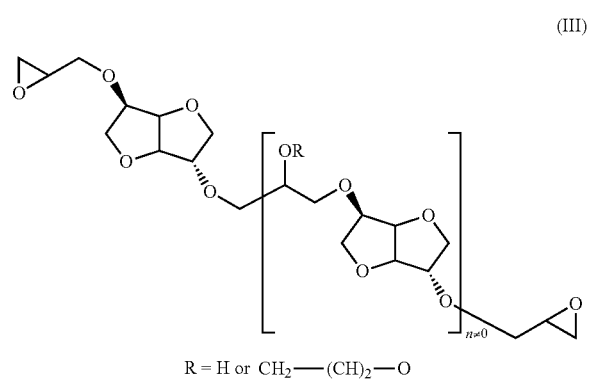

R = H or CH$_2$—(CH)$_2$—O

The presence of oligomers and/or of monoglycidyl ethers of isosorbide can be directly related to the epoxy equivalent weight, defined as the weight of resin containing one equivalent of glycidyl function. For example, isosorbide diglycidyl ether (figure II) which has a molecular weight of 258 g/mol and which contains 2 glycidyl functions has an epoxy equivalent of 129 g/eq. The higher the epoxy equivalent weight, the higher the content of oligomer and/or monoglycidyl ether of isosorbide: it will therefore be sought to minimize this epoxy equivalent.

None of the abovementioned prior art documents which target processes for preparing bis-anhydrohexitol ethers actually address this complex problem which consists in increasing the selectivity with respect to the difunctional derivatives to the detriment of the monofunctional derivatives and of the oligomers. Independently of this consideration, those skilled in the art would in any event have evaded a certain number of processes considered not to be industrially applicable since they use dangerous products such as metal hydride or sodium metal (U.S. Pat. No. 3,272,845), solvents (WO 2008/147472) or boron trifluoride (WO 2008/147473 in example 3 thereof). Furthermore, the processes based on high temperature and pressure conditions (U.S. Pat. No. 4,770,871) have the drawback of using expensive and complex devices.

Those skilled in the art would therefore have turned to methods consisting in reacting the isosorbide and epichlorohydrin at atmospheric pressure, in very slowly adding a basic reagent and in carrying out an azeotropic distillation (U.S. Pat. No. 3,041,300 and WO 2008/147473). EP 2 301 941 and WO 2008/147473 also describe such a process. Chatti et al. (2001) and Davy-Louis Versace et al. (2013) describe similar processes, but which are carried out without distillation. However, the applicant company has demonstrated, in the experimental section of the present application, that these processes result in compositions which have too high a content of monofunctional derivatives and also too high a content of oligomers or too high an epoxy equivalent.

Continuing its research through a great amount of work, the application company has managed to develop a process for producing bis-anhydrohexitol ether compositions, both free of solvents and free of other potentially dangerous compounds such as metal hydride, sodium metal or boron trifluoride. Furthermore, this process results in compositions with a very high richness in diepoxy derivatives of isosorbide compared with monoepoxy derivatives of isosorbide, and a low oligomer content or an epoxy equivalent which is advantageously lower than for the prior art compositions.

The process for producing a bis-anhydrohexitol ether composition, which is the subject of the present application, comprises the following steps:

a) bringing a dianhydrohexitol into contact with an organic halide,
b) placing the resulting mixture of dianhydrohexitol and organic halide under vacuum so as to obtain a negative pressure of between 100 mbar and 1000 mbar,
c) heating the mixture under vacuum at a temperature of between 50° C. and 120° C. and thus carrying out an azeotropic distillation,
d) then adding to said mixture a basic reagent for a period of between 1 hour and 10 hours and then continuing the azeotropic distillation,
e) recovering the bis-anhydrohexitol ether composition after a filtration step, concentration of the filtering and optionally a purification step.

As previously indicated, such a process makes it possible to obtain compositions which have a very high richness in diepoxy derivatives of isosorbide compared with monoepoxy derivatives of isosorbide, and a low oligomer content or an epoxy equivalent which is advantageously lower than for the prior art compositions.

Such a result is all the more surprising since nothing in the prior art described or suggested carrying out, under a reduced pressure, a process for synthesizing bis-anhydrohexitol ethers. On the contrary, it was indicated to carry out the process either at high pressure (U.S. Pat. No. 4,770,871) or at atmospheric pressure (all of the other documents discussed thus far).

The first step of the process according to the invention (step a) therefore consists in bringing a dianhydrohexitol into contact with an organic halide.

The dianhydrohexitol is preferentially an isohexitol, more preferentially chosen from isosorbide, isomannide and isoidide, and is, more preferentially, isosorbide.

The organic halide is preferably chosen from epibromohydrin, epifluorohydrin, epiiodohydrin and epichlorohydrin, and is, more preferentially, epichlorohydrin.

This organic halide is preferentially introduced in excess relative to the hydroxyl functions of the dianhydrohexitol. Thus, for 1 mol of dianhydrohexitol, between 2 and 10 mol of organic halide and more preferentially approximately 5 mol will preferentially be introduced.

This first step of bringing a dianhydrohexitol into contact with an organic halide (step a) is carried out in any device well known to those skilled in the art, which makes it possible to bring 2 chemical reagents into contact, and which is equipped with heating and stirring members. It may, for example, be a jacketed reactor. The device in question must also be equipped with a member which makes it possible to produce a partial vacuum and with a member which makes it possible to perform an azeotropic distillation, such as a reverse Dean-Stark apparatus surmounted by a condenser.

After this first step of bringing into contact (step a), a partial vacuum is then produced in the device by means of a vacuum pump, the corresponding negative pressure being between 100 mbar and 1000 mbar (step b). This means that the pressure in the reaction medium is equal to the difference between atmospheric pressure (1013 mbar) and the pressure claimed (between 100 mbar and 1000 mbar), i.e. a pressure of between 13 mbar and 913 mbar.

According to one embodiment, step b) is carried out in such a way as to obtain a negative pressure of between 100 and 800 mbar, in particular between 100 and 600 mbar.

During the third step of the process of the invention (step c), the mixture between the dianhydrohexitol and the organic halide is heated at a temperature of between 50° C. and 120° C.

The temperature of the heat-transfer fluid circulating in the jacket of the reactor must be regulated in such a way as to be at least equal to the boiling point of the organic halide used, in such a way as to begin the azeotropic distillation. During this first distillation phase, said distillation involves only the organic halide: in other words, only a part of the organic halide is eliminated by distillation. Moreover, the boiling point that must be taken into account is the boiling point of the organic halide under the partial pressure which reigns in the device.

By way of example, epichlorohydrin has a boiling point of 116° C. at atmospheric pressure, this boiling point being approximately equal to 80° C. under a partial vacuum of 275 mbar. In practice, the temperature used will be a temperature slightly above (approximately 3° C. above) the boiling point for the organic halide under consideration and for the negative pressure imposed.

During the fourth step of the process of the invention (step d), a basic reagent is then added to the dianhydrohexitol/organic halide mixture, for a period of between 1 hour and 10 hours.

The amount of basic reagent is preferentially the stoichiometric amount relative to the number of hydroxyl functions of the dianhydrohexitol (for example: 2 mol of sodium hydroxide for 1 mol of isosorbide). It may nevertheless be chosen to use a slight excess relative to this stoichiometry.

The basic reagent is chosen from lithium hydroxide, potassium hydroxide, calcium hydroxide and sodium hydroxide optionally in the form of an aqueous solution, and is, very preferentially, an aqueous solution of sodium hydroxide.

As soon as the basic reagent is introduced (step d), there is formation of water by reaction between the dianhydrohexitol and the organic halide, just as there may be provision of additional water by introduction of the basic reagent in the form of an aqueous solution. The distillation then involves the mixture of water and organic halide, the first being eliminated and the second returning to the reaction medium. In the case of a Dean-Stark device: the water constitutes the upper phase which is eliminated, whereas the halide in the lower part is returned to the reaction medium.

The azeotropic distillation is continued until complete elimination of the water. Thus, the reaction medium is heated for a further period of between 30 minutes and 1 hour after the end of the addition of the basic reagent.

In one preferential variant, a phase-transfer catalyst is added during the first step (step a). An even more substantial increase in the fluidity of the products produced is thus achieved, while at the same time maintaining a very high proportion of diepoxy derivatives of isosorbide relative to monoepoxy derivatives of isosorbide.

The phase-transfer catalyst is preferentially chosen from tetraalkylammonium halides, sulfates or hydrogen sulfates and more preferentially from tetrabutylammonium bromide and tetrabutylammonium iodide. The amount of phase-transfer catalyst is between 0.01% and 5%, preferentially between 0.1% and 2%, more preferentially 1% by weight relative to the dianhydrohexitol. A very notable reduction in the epoxy index is then achieved, thereby meaning that the amount of oligomers in the medium is greatly reduced.

Finally, the reaction medium is filtered in order to eliminate the salts formed during the reaction between the halide and the dianhydrohexitol, such as sodium chloride in the case of epichlorohydrin. The salts thus recovered are washed once again with epichlorohydrin. The washing waters are added to the first filtrate and then concentrated in such a way as to eliminate in particular the epichlorohydrin. The concentrating step is carried out for example by vacuum distillation, for example in a device of rotary evaporator and/or scraped film evaporator type. During this concentrating step, the crude product or bis-anhydrohexitol ether composition is gradually heated to 140° C. and the pressure is decreased to 1 mbar.

Optionally, an additional step of purification by distillation under reduced pressure (<1 mbar) can be carried out by means of a scraped-surface exchanger in order to separate the oligomers from the dianhydrohexitol diglycidyl ether. This step is distinct from that described in the previous paragraph.

Another subject of the present invention is based on the compositions that can be obtained according to the process of the invention.

A final subject of the present invention is based on the use of these compositions for producing composite materials, coatings and adhesives.

These compositions can also be used for the synthesis of vinyl ester by reaction with (meth)acrylic acids. These photo-crosslinkable monomers (vinyl esters) may then be used for the production of dental resins, boat hulls and specialty coatings.

The compositions according to the invention can be used in polycondensation reactions in order to obtain a three-dimensional network and a thermorigid material.

In this case, they can be used alone (homopolymerization reactions) or in combination with other monomers (copolymerization reactions).

Among the comonomers, mention may be made of the other epoxy derivatives, but also agents referred to as curing agents or crosslinking agents, such as amines, polyetheramines, polyamides, amidoamines, Mannich bases, anhydrides, polycarboxylic polyesters, mercaptans, phenolic resins, melamine resins, urea and phenol-formaldehyde. Catalysts of Lewis acid, tertiary amine or imidazole type can also be added to the formulation in order to initiate and/or accelerate crosslinking. The crosslinking reactions will be carried out at a temperature ranging from 5° to 260° C.

The materials, resins obtained from the bis-anhydrohexitol ether compositions, which are the subject of the present invention, are more chemically resistant and mechanically stronger and also have a higher glass transition temperature (Tg), compared with the same materials obtained with the bis-anhydrohexitol ethers according to the prior art, as demonstrated hereinafter.

EXAMPLES

Reagents

Isosorbide: Polysorb™ P product sold by the company Roquette Frères
Epichlorohydrin: sold by the company Sigma-Aldrich
Trimethylammonium bromide: sold by the company Sigma-Aldrich

Example 1: Tests According to the Prior Art 6 tests (tests 1 to 6) were carried out, during which the isosorbide and the epichlorohydrin were reacted, with the addition of an aqueous solution of sodium hydroxide, the azeotropic distillation being carried out at atmospheric pressure.

By way of example, the process for test No. 1 was carried out as below.

125 g of isosorbide (0.86 mol, 1 molar equivalent) then 395.6 g of epichlorohydrin (4.27 mol, 5 molar equivalents) were introduced into a 1-liter jacketed reactor equipped with a thermostatic heat-transfer fluid bath, with a mechanical paddle stirrer system, with a system for controlling the temperature of the reaction medium and with a reverse Dean-Stark apparatus surmounted by a condenser.

The reaction mixture is then heated to 116° C. (boiling point of epichlorohydrin=116° C. at atmospheric pressure) for 30 minutes.

136.9 g of an aqueous solution of sodium hydroxide at 50% are then gradually added (1.71 mol, 2 molar equivalents).

The addition lasts for a total of 6 h 12 min; the azeotropic distillation is continued and the water formed by reaction between the halide and the dianhydrohexitol is eliminated.

The reaction medium is filtered under vacuum in order to eliminate therefrom the sodium chloride formed over time. The salts are finally washed with epichlorohydrin which is then eliminated by evaporation under reduced pressure in a rotary evaporator.

The isosorbide diglycidyl ether composition or the composition containing predominantly isosorbide diglycidyl ether is then obtained in the form of a clear and slightly colored liquid (Brookfield viscosity at 25° C. of 19 800 mPa·s), having an epoxy equivalent of 216 g/equivalent.

Table 1 summarizes the operating conditions, and in particular:
- the amount of epichlorohydrin used, expressed as molar equivalent of epichlorohydrin relative to the number of moles of isosorbide (Mol Eq EPI);
- the amount of sodium hydroxide used, expressed as molar equivalent of sodium hydroxide relative to the number of moles of isosorbide (Mol Eq NaOH);
- the sodium hydroxide introduction time (NaOH intro time).

This table also indicates the distribution, determined by gas chromatography (GC) (as % of surface area), of the various constituents of the final product/of the final composition.

In all the examples of the present application, the GC analysis was carried out on a DB1 capillary column (30 m×0.32 mm), film thickness of 0.25 µm). The quantification of the species consists in calculating the relative proportion of the areas of the peaks of the chromatogram, the % of each species (x) being equal to the area of the peak of the species (x) divided by the sum of the area of all the peaks.

Example 2: Tests According to the Invention 4 tests according to the invention (tests 7 to 10) were carried out, during which the isosorbide and the epichlorohydrin were reacted, with the addition of an aqueous solution of sodium hydroxide, the azeotropic distillation being carried out under a partial vacuum.

By way of example, the process for test No. 7 was carried out as below.

125 g of isosorbide (0.86 mol, 1 molar equivalent) then 395.6 g of epichlorohydrin (4.27 mol, 5 molar equivalents) are introduced into a 1-liter jacketed reactor, equipped with a thermostatic heat-transfer fluid bath, equipped with a mechanical paddle stirrer system, with a system for controlling the temperature of the reaction medium and with a reverse Dean-Stark apparatus surmounted by a condenser.

The system is brought to a pressure of 568 mbar relative. The reaction mixture is then heated to 100° C. (boiling point=100° C. at 568 mbar) for 30 minutes before beginning the controlled addition of 136.9 g of an aqueous solution of sodium hydroxide at 50% (1.71 mol, 2 molar equivalents). The addition lasts for a total of 3 h 5 min. The water is continuously eliminated by azeotropic distillation.

The reaction medium is filtered under vacuum in order to remove therefrom the sodium chloride formed over time. The salts are washed with epichlorohydrin which is then eliminated by evaporation under reduced pressure in a rotary evaporator.

The isosorbide diglycidyl ether composition or the composition containing predominantly isosorbide diglycidyl ether is then obtained in the form of a clear liquid (Brookfield viscosity at 25° C. of 13 900 mPa·s), having an epoxy equivalent of 200 g/equivalent.

Example 3: Tests According to the Invention with the Use of a Phase-Transfer Catalyst 6 other tests according to the invention (tests 11 to 16) were carried out, during which the isosorbide and the epichlorohydrin were reacted in the presence of a phase-transfer catalyst, with the addition of an aqueous solution of sodium hydroxide, the azeotropic distillation being carried out under a partial vacuum.

By way of example, the process for test No. 11 was carried out as below.

125 g of isosorbide (0.86 mol, 1 molar equivalent), 395.6 g of epichlorohydrin (4.27 mol, 5 molar equivalents) then 1.25 g of triethylammonium bromide (1% by weight relative to the isosorbide) are introduced into a 1-liter jacketed reactor, heated by means of a thermostatic heat-transfer fluid bath, equipped with a mechanical paddle stirrer system, with a system for controlling the temperature of the reaction medium and with a reverse Dean-Stark apparatus surmounted by a condenser.

The system is brought to a pressure of 275 mbar relative. The reaction mixture is heated to 80° C. (boiling point=80° C. at 275 mbar) before beginning the controlled addition of 136.9 g of an aqueous solution of sodium hydroxide at 50% (1.71 mol, 2 molar equivalents). The addition lasts for a total of 2 h 50 min. The water is then continuously eliminated by azeotropic distillation.

The reaction medium is filtered under vacuum in order to eliminate therefrom the sodium chloride formed over time and the catalyst. The salts are washed with epichlorohydrin which is then eliminated by evaporation under reduced pressure in a rotary evaporator.

The isosorbide diglycidyl ether composition or the composition containing predominantly isosorbide diglycidyl ether is then obtained in the form of a clear liquid (Brookfield viscosity at 25° C. of 4350 mPa·s) having an epoxy equivalent of 176 g/equivalent.

Table 2 summarizes the operating conditions used for tests 7 to 16, and in particular:

the amount of epichlorohydrin used, expressed as molar equivalent of epichlorohydrin relative to the number of moles of isosorbide (Mol Eq EPI);

the amount of sodium hydroxide used, expressed as molar equivalent of sodium hydroxide relative to the number of moles of isosorbide (Mol Eq NaOH);

the sodium hydroxide introduction time (NaOH intro time);

the negative pressure (mbar);

the nature of the catalyst.

This table also indicates the distribution, determined by GC (as % of surface area), of the various constituents of the final product.

Comparison between table 1 and table 2 demonstrates that the process according to the invention makes it possible to obtain compositions in which the proportion of isosorbide diglycidyl ether relative to the isosorbide monoglycidyl ether is considerably larger and the epoxy equivalent and therefore the content of parasitic oligomers produced is lower.

Finally, the preferred variant of the invention consisting in using a phase-transfer catalyst makes it possible to exacerbate these effects. Tests Nos. 11 to 15 which use 1% by weight of catalyst make it possible in particular to very substantially decrease the epoxy equivalent, and therefore to cause the oligomer content to drop.

TABLE 1

| | Test No. | | | | | |
|---|---|---|---|---|---|---|
| | 1 | 2 | 3 | 4 | 5 | 6 |
| Mol Eq EPI | 5 | 5 | 5 | 10 | 10 | 10 |
| Mol Eq NaOH | 2 | 2 | 2 | 2 | 2 | 2 |
| NaOH intro time | 6 h 12 | 3 h 06 | 1 h 04 | 9 h 37 | 6 h 12 | 3 h 08 |
| isosorbide | 0.4% | 0.1% | 0.0% | 1.0% | 0.3% | 0.1% |
| isosorbide monoglycidyl ether | 18.7% | 13.4% | 14.1% | 33.7% | 28.7% | 28.5% |
| isosorbide diglycidyl ether | 40.8% | 49.2% | 44.7% | 30.8% | 38.0% | 40.9% |
| diisosorbide monoglycidyl ether | 4.5% | 3.4% | 4.2% | 6.1% | 5.0% | 4.6% |
| diisosorbide diglycidyl ether | 10.8% | 14.9% | 15.6% | 9.0% | 10.1% | 10.3% |
| glycerol | 0.5% | 0.3% | 0.6% | 0.6% | 0.3% | 0.2% |
| others | 24.3% | 18.7% | 20.8% | 18.8% | 17.6% | 15.4% |
| % isosorbide diglycidyl ether/(isosorbide mono + diglycidyl ether) | 68.6% | 78.5% | 76.0% | 47.8% | 57.0% | 58.9% |
| Epoxy equivalent (g/eq) | 215 | 216 | 216 | 234 | 224 | 224 |

TABLE 2

| | Test No. | | | | | | | | | |
|---|---|---|---|---|---|---|---|---|---|---|
| | 7 | 8 | 9 | 10 | 11 | 12 | 13 | 14 | 15 | 16 |
| Mol Eq EPI | 5 | 10 | 5 | 5 | 5 | 5 | 10 | 5 | 5 | 5 |
| Mol Eq NaOH | 2 | 2 | 2 | 2 | 2 | 2 | 2 | 2 | 2 | 2 |
| NaOH intro time | 3 h 05 | 3 h 09 | 4 h 30 | 2 h 56 | 2 h 50 | 3 h 00 | 2 h 54 | 3 h 02 | 3 h 04 | 2 h 55 |
| Pressure (mbar) | 568 | 275 | 275 | 192 | 275 | 275 | 275 | 275 | 275 | 275 |
| catalyst | — | — | — | — | TEAB | TEAB | TEAB | TEAC | TBAI | TEAB* |
| isosorbide | 0.1% | 0.1% | 0.0% | 0.2% | 0.0% | <0.1% | 0.0% | <0.1% | 0.0% | 0.0% |
| isosorbide monoglycidyl ether | 12.6% | 8.6% | 4.2% | 4.8% | 5.1% | 10.1% | 11.7% | 10.4% | 6.4% | 4.5% |
| isosorbide diglycidyl ether | 57.0% | 60.7% | 65.8% | 58.1% | 63.0% | 63.9% | 66.3% | 56.0% | 64.2% | 61.6% |
| diisosorbide monoglycidyl ether | 2.4% | 1.1% | 0.6% | 0.8% | 1.0% | 1.7% | 1.0% | 2.3% | 1.0% | 0.9% |
| diisosorbide diglycidyl ether | 14.5% | 12.6% | 13.1% | 15.8% | 12.5% | 12.4% | 9.3% | 14.4% | 13.4% | 15.4% |
| glycerol | 0.2% | <0.1% | 0.1% | 0.2% | 0.0% | <0.1% | 0.0% | 0.1% | <0.1% | 0.0% |
| others | 13.2% | 16.8% | 16.2% | 20.1% | 18.4% | 11.7% | 11.7% | 16.7% | 14.9% | 17.6% |
| isosorbide diglycidyl ether/(isosorbide mono + diglycidyl ether) | 81.9% | 87.6% | 94.0% | 92.4% | 92.5% | 86.4% | 85.0% | 84.3% | 90.9% | 93.2% |
| epoxy equivalent (g/eq) | 200 | 203 | 211 | 209 | 176 | 178 | 179 | 187 | 181 | 195 |

*tests 11 to 15 are carried out with 1% by weight of transfer agent, whereas test 16 uses only 0.1% of this agent
TEAB: Triethylammonium bromide
TEAC: Triethylammonium chloride
TBAI: Triethylammonium iodide

Example 4: Production of Resins from Compositions According to the Invention or According to the Prior Art Epoxy resins were prepared from the isosorbide glycidyl ether compositions and in the presence of a curing agent of amine type (isophorone diamine).

The amount of isophorone diamine introduced is calculated in such a way that the ratio of the number of —NH groups to the number of epoxy groups is equal to 1. The isophorone diamine is available under the brand name Vestamid® IPD from Evonik. The —NH group weight equivalent is 42.5 g/eq. The formula used to calculate the uses of diamine is the following:

$$m(\text{isophorone diamine}) = \frac{m epoxy \times 42.5}{\text{epoxy equivalent}}$$

By way of example, the process for test 17 was as below.

10.630 g of the product obtained in test No. 2 are mixed at ambient temperature with 1.934 g of isophorone diamine for 1 minute. The mixture, which is homogeneous and flows at ambient temperature, is placed in a silicone mold (L=43 mm, W=20 mm). The crosslinking is carried out in an oven for 1 hour at 80° C. and 2 h at 180° C.

A material which is solid at ambient temperature and which has a glass transition temperature (Tg) of 66° C. is then obtained. The glass transition temperature is measured by DSC at the second passage of a temperature ramp of −100 to 200° C. at 10° C./min.

Table 3 summarizes the results obtained according to the isosorbide glycidyl ether compositions used.

TABLE 3

| Test No. | 17 | 18 | 19 | 20 |
| --- | --- | --- | --- | --- |
| Ref of the test corresponding to the isosorbide glycidyl ether used | 4 (outside the invention) | 5 (outside the invention) | 13 (according to the invention) | 15 (according to the invention) |
| Epoxy equivalent (g/eq) | 234 | 224 | 179 | 181 |
| Tg (° C.) | 66 | 75.2 | 94.5 | 99.4 |

A very clear increase in the glass transition temperature is noted for tests 19 and 20, carried out with the compositions according to the invention, compared with tests 17 and 18 which use compositions according to the prior art.

The invention claimed is:

1. A process for producing bis-anhydrohexitol ether compositions, comprising the following steps:
    a) bringing a dianhydrohexitol into contact with an organic halide,
    b) placing the resulting mixture of dianhydrohexitol and organic halide under vacuum so as to obtain a negative pressure of between 100 mbar and 1000 mbar,
    c) heating the mixture under vacuum at a temperature of between 50° C. and 120° C. and thus carrying out an azeotropic distillation,
    d) then adding to said mixture a basic reagent for a period of between 1 hour and 10 hours and then continuing the azeotropic distillation,
    e) recovering the bis-anhydrohexitol ether composition after a filtration step, concentration of the filtering and optionally a purification step.

2. The process as claimed in claim 1, wherein the dianhydrohexitol comprises one of isosorbide, isomannide and isoidide.

3. The process as claimed in claim 1, wherein the organic halide is chosen from epibromohydrin, epifluorohydrin, epiiodohydrin and epichlorohydrin.

4. The process as claimed in claim 1, wherein the basic reagent is chosen from lithium hydroxide, potassium hydroxide, calcium hydroxide and sodium hydroxide optionally in the form of an aqueous solution.

5. The process as claimed in claim 1, wherein a phase-transfer catalyst is added during step a).

6. The process as claimed in claim 5, wherein the phase-transfer catalyst is chosen from tetrabutylammonium halides or sulfates.

7. The process as claimed in claim 5, wherein the amount of phase-transfer catalyst is between 0.01% and 5% by weight relative to the dianhydrohexitol.

8. A bis-anhydrohexitol ether composition obtained according to the process of claim 1.

9. The process as claimed in claim 5, wherein the phase-transfer catalyst is hydrogen sulfate.

* * * * *